United States Patent
Chen et al.

(10) Patent No.: US 9,321,795 B2
(45) Date of Patent: Apr. 26, 2016

(54) USE OF HYDROXYCINNAMALDEHYDE GLYCOSIDE DERIVATIVES FOR TREATING GLOMERULONEPHRITIS

(71) Applicant: National Defense Medical Center, Taipei (TW)

(72) Inventors: Ann Chen, Taipei (TW); Shuk-Man Ka, Taipei (TW); Kuo-Feng Hua, I-Lan (TW); Shui-Tein Chen, Taipei (TW); Kuo-Ping Chao, Chiayi County (TW)

(73) Assignee: National Defense Medical Center, Taipei (TW)

( * ) Notice: Subject to any disclaimer, the term of this patent is extended or adjusted under 35 U.S.C. 154(b) by 0 days.

(21) Appl. No.: 14/693,619

(22) Filed: Apr. 22, 2015

(65) Prior Publication Data

US 2015/0299242 A1    Oct. 22, 2015

(30) Foreign Application Priority Data

Apr. 22, 2014  (TW) .............................. 103114584 A (51) Int. Cl.
| | |
|---|---|
| *C07H 15/203* | (2006.01) |
| *A61K 31/7034* | (2006.01) |
| *A61K 45/06* | (2006.01) |

(52) U.S. Cl.
CPC .......... *C07H 15/203* (2013.01); *A61K 31/7034* (2013.01); *A61K 45/06* (2013.01)

(58) Field of Classification Search
None
See application file for complete search history.

(56) References Cited

PUBLICATIONS

Daubresse, et al., Synthesis, 2:157 (1998) [p. 157 only].*

* cited by examiner

*Primary Examiner* — Michael Barker
(74) *Attorney, Agent, or Firm* — WPAT, P.C., INTELLECTUAL PROPERTY ATTORNEYS; Anthony King (57) ABSTRACT

The present invention relates to a new use of a cinnamaldehyde derivative of formula (I) for treating glomerulonephritis (GN). Particularly, the present invention discloses that the cinnamaldehyde derivative of formula (I) is effective in treating glomerulonephritis (GN), which can alleviate various symptoms and signs of GN, including reducing proteinuria, serum blood urea nitrogen (BUN), glomerular cell proliferation, and renal macrophage/lymphocyte infiltration, etc.

9 Claims, 10 Drawing Sheets

USE OF HYDROXYCINNAMALDEHYDE GLYCOSIDE DERIVATIVES FOR TREATING GLOMERULONEPHRITIS

RELATED APPLICATIONS

This application claims the benefit of Taiwanese Patent Application No. 103114584, filed on Apr. 22, 2014, the entire content of which is incorporated herein by reference.

TECHNOLOGY FIELD

The present invention relates to use of hydroxycinnamaldehyde glycoside derivatives for treating glomerulonephritis. Namely, the present invention discloses the effect of hydroxycinnamaldehyde glycoside derivatives in treating glomerulonephritis, which ameliorates symptoms of glomerulonephritis including reducing Proteinuria, glomerular cell proliferation and lymphocyte infiltration.

BACKGROUND OF THE INVENTION

Glomerulonephritis (GN) generally refers to a kidney tissue lesion which manifests with the appearance of immunoreaction or inflammatory response in the glomerulus. Generally, it is not caused by a direct infection of the glomerulus itself, but some induced inflammatory response caused by the immune complex induced by the infection in other parts of the body or autoimmune disease which deposits in the glomerulus through blood circulation which results in the damage of the glomerulus. Glomerulonephritis is one of the main causes of chronic kidney disease (CDK). If not treated in time, it is likely to develop into chronic renal failure, which ultimately will result in the loss of function of the kidney and entering of the end-stage renal disease.

The characteristics of clinical manifestation of glomerulonephritis are mainly hematuria and proteinuria. In addition, macrophage infiltration in the kidney tissue is generally observed. Relative research believes that macrophages express many pro-inflammation cytokines and chemokines such as TNF-α, IL-1β, IL-6, IL-18, IL-23, MIP-1, MIP-2 and MCP-1 etc., which are simultaneously involved in oxidative stress response. Moreover, activated macrophages secrete matrix metallopeptidase 9 (MMP9), which leads to the transformation of epithelial cells to mesenchymal cells, causing sclerosis of the kidney tissue. Currently there are researches focusing on macrophage to develop treatment for glomerulonephritis, such as using drugs or vaccine to disrupt the accumulation of macrophages in the kidney, or even using gene modification to reduce macrophage activity to reduce the damage in the kidney.

Generally, immunosuppressors such as steroid or cyclosporine have been used for the treatment of glomerulonephritis, but they often cause severe side effects. In recent years, angiotensin converting enzyme inhibitor (ACEi) or angiotensin receptor blocker (ARB) are also used for the treatment to delay the progression of the kidney disease. However, some reports have indicated that long-term use of such drugs can possibly cause progression of kidney dysfunction, particularly in patients with renal arterial stenosis.

*Cinammomum osmophloeum* Kaneh is an evergreen woody plant that is epidemic to Taiwan, which its branches, leaves and bark are enriched with essential oil. The extracted oil has similar ingredients as cinnamon oil, being mainly cinnamalydehyde (80%), salicylic acid and eugenol, wherein cinnamalydehyde has been proven to have many curative effects such as anti-tumor (*Cancer Lett*, 196: 143-152, 2003), anti-inflammation (*Food Chem Toxicol*, 46: 220-231, 2008; *Eur J Pharmacol*, 537: 174-180, 2006; *Biochem Pharmacol*, 75: 494-502, 2008; *Mediators Inflamm*, 2010: 529359, 2010), anti-bacteria (*Toxicol Appl Pharmacol*, 244: 174-180, 2010), anti-oxidation (*Cancer Lett*, 196: 143-152, 2003; *Biochem Pharmacol*, 69: 791-799, 2005.) and can regulate blood glucose and blood lipid through regulating the activity of saccharide transport proteins and modifying insulin's functions (*Food Chem Toxicol*, 48: 2344-2349, 2010; *Phytomedicine*, 14: 15-22, 2007; *Biochimie*, 93: 339-344, 2010.), while it can also regulate platelet agglutination and lower the amount of uric acid in urine (*Toxicol Appl Pharmacol*, 244: 174-180, 2010). Previous studies also showed that cinnamaldehyde has a certain level of cytotoxicity to cells. Until today, no literatures have reported a cinnamaldehyde derivative having renoprotective effects in treating or ameliorating symptoms of glomerulonephritis.

BRIEF SUMMARY OF THE INVENTION

The present invention is based on the unexpected finding that the hydroxycinammaldehde glycoside derivative with the structure of formula (I) is effective in alleviating the symptoms of glomerulonephritis (GN). Therefore, the present invention provides a new approach for treatment of glomerulonephritis (GN) in a subject.

In particular, the present invention provides a method for treating glomerulonephritis (GN) in a subject in need thereof, which comprises administering a therapeutically effective amount of a hydroxycinammaldehde glycoside derivative with the structure of formula (I) to the subject. The present invention also provides a hydroxycinammaldehde glycoside derivative with the structure of formula (I).

The hydroxycinammaldehde glycoside derivative has the structure below:

Formula (I)

wherein R is a hexose or pentose moiety, which is not modified or is further modified by oxidation, deoxidation, alkylation or acylation.

In some embodiments, R is a glucose, fructose, galactose, rhamnose, ribose or glucuronic acid group.

In one embodiment, the hydroxycinammaldehde glycoside derivative of formula (I) in the present invention can be used to alleviate or reduce kidney tissue lesions in glomerulonephritis, including glomerular cell proliferation, lymphocyte filtration and kidney tissue fibrosis.

In another embodiment, the hydroxycinammaldehde glycoside derivative of formula (I) in the present invention can be used to alleviate or reduce symptoms of glomerulonephritis, including proteinuria or serum blood urea nitrogen (BUN).

In some embodiments, the hydroxycinammaldehde glycoside derivative is administered in combination with one or more therapeutic agents for treating glomerulonephritis known in the art, including but not limited to corticosteroid drugs, non-steriodal anti-inflammatory drugs (NSAIDs), immunosuppressants, cytotoxic drugs and vasodilators.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

For the purpose of illustrating the invention, there are shown in the drawings embodiments which are presently preferred. It should be understood, however, that the invention is not limited to the illustrated preferred embodiments. In the drawings.

DETAILED DESCRIPTION OF THE INVENTION

Unless defined otherwise, all technical and scientific terms used herein have the same meanings as is commonly understood by one of skill in the art to which this invention belongs. If a conflict appears, one should base on this document, including the definitions therein.

As used herein, the articles "a" and "an" refer to one or more than one (i.e., at least one) of the grammatical object of the article. By way of example, "an element" means one element or more than one element.

The present invention provides a hydroxycinammaldehde glycoside derivative of formula (I). In the present invention, it is unexpectedly found that administering the hydroxycinammaldehde glycoside derivative of formula (I) to glomerulonephritis (GN) mice can treat glomerulonephritis and alleviate its symptoms and exert excellent renoprotective effects by effectively improving or alleviating proteinuria, improving kidney function, reducing inflammatory cell infiltration and tissue fibrosis condition.

Therefore, the present invention provides a therapeutic approach to treat or ameliorate certain pathological and physiological symptoms of GN. The present invention also provides a hydroxycinammaldehde glycoside derivative of formula (I).

The hydroxycinammaldehde glycoside derivative in the present invention, its chemical name being 4-hydroxyphenylacrylaldehyde glycoside, has the following structure:

Formula (I)

wherein R is a hexose or pentose moiety, which is not modified or is further modified by oxidation, deoxidation, alkylation or acylation.

The term "a hexose or pentose moiety" as described in the present invention indicates a hexose or pentose group linked to the main structure of formula (I) through a glycosidic linkage. Embodiment of the sugar moiety includes but is not limited to glucose, fructose, galactose, rhamnose and ribose group. The sugar moiety can include one or more modifications known in the art, such as oxidation, deoxidation, alkylation or acylation. In some embodiments, the sugar moiety is oxidized on the hydroxyl group of the saccharide structure, forming carboxylic acids. For example, glucose is oxidized on its hydroxyl group forming glucuronic acid, forming glucuronide in the structure of formula (I).

The hydroxycinammaldehde glycoside derivative of formula (I) used in the present invention can be obtained through extracting cinnamaldehyde from natural plant products and modified by glycosylation. Extraction can be performed from natural plant products, including but are not limited to, leaves of *Cinnamomum cassia* or *Cinammomum osmophloeum*

Kaneh. For example, using water distillation to extract cinnamon oil from *Cinammomum osmophloeum* Kaneh leaves, determining its composition with gas chromatography-mass spectrometry (GC-MS), using semi-preparative HPLC to purify its cinnamaldehyde component, and identifying its chemical composition through nuclear magnetic resonance (NMR) (*Food Chem Toxicol*, 46: 220-231, 2008; *J Agric Food Chem*, 53: 7274-7278, 2005). Then the obtained cinnamaldehyde is glycosylated to obtain the hydroxycinammaldehde glycoside derivative used in the present invention. As shown in example 1.2, Scheme 1 shows the synthesis of the hydroxycinammaldehde glycoside derivative with R being glucose in formula (I), wherein the starting materials can be replaced with trichloroacetimidate derivatives with a different sugar moiety, so as to obtain the hydroxycinammaldehde glycoside derivative with a different R species in formula (I). In some embodiments, R in the structure of formula (I) can be a hexose group or a pentose group, which includes but is not limited to glucose, fructose, galactose, rhamnose and ribose.

The glomerulonephritis (GN) as described herein generally refers to the kidney lesion disease where immune or inflammatory response appears in the glomeruli, accompanied with acute nephritis or nephritic syndromes. Clinical manifestation of glomerulonephritis are mainly hematuria and proteinuria, while macrophage infiltration in kidney tissue is commonly observed.

In the examples of the present invention, it is found in GN animal model experiments that the following effects can be achieved by administering the hydroxycinammaldehde glycoside derivative of formula (I): (1) alleviating kidney function and proteinuria; (2) suppressing lymphatic T cell activation; (3) preventing glomerular cell proliferation and inflammatory cell infiltration; (4) suppressing downstream inflammatory cytokine production caused by NLRP3 inflammasome; (5) further achieving NF-κB activation suppression effect by mediating TLR4 pathway. In glomerulonephritis animal model and macrophage cell model, the hydroxycinammaldehde glycoside derivative of formula (I) of the present invention can reduce NLRP3 inflammasome activation by immunomodulation and being involved in TLR4-MyD88-NF-κB activation pathway to achieve anti-inflammatory effects.

When the hydroxycinammaldehde glycoside derivative is described as isolated or purified in the present invention, it should be understood as not absolutely isolated or purified, but relatively isolated or purified. For example, purified hydroxycinammaldehde glycoside derivative refers to one that is more purified compared to its naturally existing form. In one embodiment, a preparation comprising purified hydroxycinammaldehde glycoside derivative may comprise this compound in an amount of more than 50%, more than 60%, more than 70%, more than 80%, more than 90%, or 100% (w/w) of the total preparation. It should be understood that when a certain number was used herein to show a ratio or dosage, said number generally includes dosages within the range of 10% more and less, or more specifically, the scope of 5% more and less than the number.

The term "individual" or "subject" used herein includes human and non-human animals such as companion animals (such as dogs, cats and the like), farm animals (such as cows, sheep, pigs, horses and the like), or laboratory animals (such as rats, mice, guinea pigs and the like).

The term "treating" as used herein refers to the application or administration of a composition including one or more active agents to a subject afflicted with a disorder, a symptom of the disorder, or a progression of the disorder, with the purpose to cure, heal, alleviate, relieve, alter, remedy, ameliorate, improve, or affect the disorder, the symptoms of the disorder, the disabilities induced by the disorder, or the progression of the disorder.

The term "therapeutically effective amount" used herein refers to the amount of an active ingredient to confer a therapeutic effect in a treated subject. For example, an effective amount for glomerulonephritis is an amount that can prohibit, improve, alleviate or reduce one or more symptoms such as reducing proteinuria or reducing serum blood urea nitrogen (BUN) or reducing creatinine (Cr) content. The symptoms may be determined and evaluated using methods known in the art based on various disease progress-related indexes, for example by analyzing the amount of urine protein, blood urea nitrogen or serum creatinine, or by analyzing renal sections. The therapeutically effective amount may change depending on various reasons, such as administration route and frequency, body weight and species of the individual receiving said pharmaceutical, and purpose of administration.

Persons skilled in the art may determine the dosage in each case based on the disclosure herein, established methods, and their own experience. For example, in certain embodiments, the oral dosage of osthole used in the present invention is 1 to 1,000 mg/kg daily, specifically 5 to 500 mg/kg daily, more specifically 10 to 250 mg/kg daily, even more specifically 20 to 175 mg/kg daily. One or more administrations can be done daily depending on the need.

According to the present invention, the hydroxycinammaldehde glycoside derivative of formula (I) may be used as an active ingredient for treating glomerulonephritis. In one embodiment, a therapeutically effective amount of the active ingredient may be formulated with a pharmaceutically acceptable carrier into a pharmaceutical composition of an appropriate form for the purpose of delivery and absorption. Depending on the mode of administration, the pharmaceutical composition of the present invention preferably comprises about 0.1% by weight to about 100% by weight of the active ingredient, wherein the percentage by weight is calculated based on the weight of the whole composition.

As used herein, "pharmaceutically acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. Some examples of appropriate excipients include lactose, dextrose, sucrose, sorbose, mannose, starch, Arabic gum, calcium phosphate, alginates, tragacanth gum, gelatin, calcium silicate, microcrystalline cellulose, polyvinyl pyrrolidone, cellulose, sterilized water, syrup, and methylcellulose. The composition may additionally comprise lubricants, such as talc, magnesium stearate, and mineral oil; wetting agents; emulsifying and suspending agents; preservatives, such as methyl and propyl hydroxybenzoates; sweeteners; and flavoring agents. The composition of the present invention can provide the effect of rapid, continued, or delayed release of the active ingredient after administration to the patient.

According to the present invention, the form of said composition may be tablets, pills, powder, lozenges, packets, troches, elixers, suspensions, lotions, solutions, syrups, soft and hard gelatin capsules, suppositories, sterilized injection fluid, and packaged powder.

The composition of the present invention may be delivered via any physiologically acceptable route, such as oral, parenteral (such as intramuscular, intravenous, subcutaneous, and intraperitoneal), transdermal, suppository, and intranasal methods. Regarding parenteral administration, it is preferably used in the form of a sterile water solution, which may comprise other substances, such as salts or glucose sufficient to make the solution isotonic to blood. The water solution may be appropriately buffered (preferably with a pH value of 3 to 9) as needed. Preparation of an appropriate parenteral composition under sterile conditions may be accomplished with standard pharmacological techniques well known to persons skilled in the art, and no extra creative labor is required.

According to the present invention, the hydroxycinammaldehde glycoside derivative of formula (I) or compositions comprising the hydroxycinammaldehde glycoside derivative of formula (I) as the active ingredient may be used in treating individuals with glomerulonephritis. Specifically, the hydroxycinammaldehde glycoside derivative of formula (I) or compositions comprising the hydroxycinammaldehde glycoside derivative of formula (I) as the active ingredient may be administered to individuals with glomerulonephritis or individuals with the risk of acquiring glomerulonephritis so as to prevent occurrence of the disease or improve the symptoms or delay deterioration of the symptoms.

According to the present invention, the hydroxycinammaldehde glycoside derivative of formula (I) or compositions comprising the hydroxycinammaldehde glycoside derivative of formula (I) as the active ingredient may be used in combination with existing therapeutic methods or medicaments, such as plasmapheresis or protein adsorption, or pharmaceutical treatment, including but not limited to corticosteroids (such as prednisolone), non-steriodal anti-inflammatory drugs (NSAIDs), cytotoxic drugs (such as cyclophosphamide, chlorambucil, and azathioprine), immunosuppressants (such as cyclosporine and Mycophenolate Mofetil), and vasodilators (such as angiotensin-converting-enzyme inhibitors (ACE inhibitors)). In one embodiment, the medicament or therapeutic method used in combination may be used simultaneously (parallel) or sequentially. When medicaments are used in combination, the medicaments may be mixed in the same formula or put in different formulas separately, such as separate capsules, pills, tablets, and injections.

The present invention is further illustrated by the following examples, which are provided for the purpose of demonstration rather than limitation.

EXAMPLES

1. Materials and Methods
1.1 Mouse Nephritis Model

Experiments were performed on 8-week-old female C57BL/6 mice. The mice were separated into 3 groups at 8-weeks old. One of the groups were injected intravenously with normal saline to be used as normal controls, where the pathological control group and the GN disease treatment group by the cinnamaldehyde derivative of the invention were intraperitoneally injected with 20 g *Salmonella* LPS (Sigma, USA) (*Am J Physiol Renal Physiol*, 296: F1088-1099, 2009; *Nephron*, 84: 167-176, 2000; *Nephron Exp Nephrol*, 112: e81-91, 2009) twice a week, continuously for 7 weeks for disease induction. Starting two days before disease induction, the GN disease treatment group was intraperitoneally injected with the cinnamaldehyde derivative of the invention at a daily dose of 30 mg/ml for continuous 7 weeks, while the pathological control group was given placebo daily through intraperitoneal injection. Urine samples were collected in metabolic cages every week. Mice were sacrificed on $7^{th}$ week after the disease induction. Blood, kidneys, spleen and liver were collected and stored properly for further analysis.

1.2 Hydroxycinammaldehde Glycoside Derivative

The cinnamaldehyde derivative used in the present invention was obtained through modification with saccharide groups of the cinnamaldehyde obtained through *Cinammomum osmophloeum* Kaneh extraction.

First of all, water distillation was used to extract cinnamon oil from *Cinammomum osmophloeum* Kaneh leaves, its composition determined by gas chromatography-mass spectrometry (GC-MS), its cinnamaldehyde component purified using semi-preparative HPLC, and its chemical composition identified through nuclear magnetic resonance (NMR) (*Food Chem Toxicol*, 46: 220-231, 2008; *J Agric Food Chem*, 53: 7274-7278, 2005). Then the obtained cinnamaldehyde was glycosylated and its structure was identified.

Synthetization of 4-hydroxyphenylacrylaldehyde glycoside (5)

The synthetic strategy for the synthesis of 4-hydroxyphenylacrylaldehyde glycoside 5 is shown in Scheme 1 involved a three-step synthetic route from trichloroacetimidate derivative 1. Trichloroacetimidate derivative 1 was prepared from 2,3,4,6-tetra-O-acetyl-D-glucopyranose according to Schmidt's trichloroacetimidate procedure. $BF_3$-promoted glycosylation of 1 using 4-hydroxybenzaldehyde afforded compound 2 in 42% yield. Subsequently, compound 2 was treated with triphenyl-1,3-dioxolan-2-ylmethylphosphonium bromide 3 and potassium tert-butoxide in THF to afford a strong predominance of the E isomer of styryl-1,3-dioxolane glycoside 4. Styryl-1,3-dioxolane glycoside 4 was then removed the acetyl groups by using sodium methoxide in methanol, followed by neutralization of the reaction mixture with a mild acid to obtain acrylaldehyde glycoside 5 in 77% yield.

Scheme 1: Synthesis of 4-hydroxyphenylacrylaldehyde glycoside 5 (HCAG).

Chemistry. All reactions were conducted in dried glassware under an oven at 120° C. overnight. All reagents were used as received from commercial suppliers unless otherwise stated. Dichloromethane, chloroform, and methanol were distilled over $CaH_2$ under nitrogen. Chloroform-d and DMSO-$d_6$ of spectrograde were used as solvents. All NMR chemical shifts were reported as values in parts per million (ppm), and coupling constants (J) were given in hertz (Hz). The splitting pattern abbreviations are as follows: s, singlet; d, doublet; t, triplet; m, unresolved multiplet due to the field strength of the instrument; dd, doublet of doublet. Purification was performed by using preparative separations in flash column chromatography (Merck silica gel 60, particle size of 230-400 mesh). Analytical TLC was carried out on precoated plates (Merck silica gel 60, F254). Compounds analyzed on the TLC plates were visualized by using UV light, $I_2$ vapor, or 2.5% phosphomolybdic acid in ethanol with heating.

4-(2,3,4,6-Tetra-O-acetyl-D-glucopyranosyloxy)benzaldehyde (2)

2,3,4,6-Tetra-O-acetyl-α-D-galactopyranosyl 2,2,2-trichloroacetimidate 1 (9.85 g, 20 mmol) and 4-hydroxybenzaldehyde (3.66 g, 30 mmol) were dissolved in $CH_2Cl_2$ (100 mL) and then the reaction mixture was cooled to −20° C. Boron trifluoride diethyl etherate (46%, 16 mL, 60 mmol) was added dropwise at this temperature. The reaction mixture was stirred at −20° C. for 4 h and was monitored by TLC. Saturated $NaHCO_3$ aqueous solution (150 mL) was added to the mixture. The aqueous layer was separated and extracted with $CH_2Cl_2$ (2×150 mL). The organic layers were combined, dried over $MgSO_4$ and concentrated. Purification by silica gel column chromatography yielded 2 (3.8 g, 42%) as a white solid.

4-(2,3,4,6-Tetra-O-acetyl-D-glucopyranosyloxy)-(E)-2-styryl-1,3-dioxolane (4)

4-(2,3,4,6-Tetra-O-acetyl-D-glucopyranosyloxy)benzaldehyde 2 (3.4 g, 7.5 mmol) was dissolved in THF (75 mL), potassium tert-butoxide (0.84 g, 7.5 mmol) and (1,3-dioxolan-2-ylmethyl)triphenylphosphonium bromide 3 (3.95 g, 9.2 mmol) was added portionwise. The reaction mixture was heated to reflux for 10 h. After completion of the reaction, the mixture was added water and extracted with $CH_2Cl_2$ (2×100 mL). Organic layers were combined, dried over $MgSO_4$ and concentrated. The residue was purified by silica gel column chromatography to yield 4 (2.5 g, 64%) as a white powder.

4-hydroxyphenylacrylaldehyde glycoside (5)

Compound 4 (1.8 g, 3.4 mmol) was dissolved in dry MeOH (40 mL) and NaOMe in MeOH was added at 0° C. The solution was stirred at room temperature for 3 h. The progress of this reaction was monitored by TLC. The reaction mixture was concentrated in vacuum and purified by sephadex LH-20 column chromatography to yield a pale yellow powder. The pale yellow powder (1.1 g) in $CH_3OH$ (20 mL) was added $H_2O$ (10 mL) and HOAc (10 mL) at 0° C. The mixture was then warmed up to room temperature and stirred for 10 h. Saturated aqueous $NaHCO_3$ solution was added, and the aqueous layer was extracted with $CH_2Cl_2$ (2×50 mL). Organic layers were combined, dried over $MgSO_4$ and evaporated to give a yellow powder 5. (0.8 g, 77% under a two-step process), its $^1$HNMR (DMSO-$d_6$): 9.61 (d, J=7.8 Hz, 1H), 7.70 (d, J=8.4 Hz, 2H), 7.67 (d, J=15.6 Hz, 1H), 7.09 (d, J=8.4 Hz, 2H), 5.18 (d, J=5.4 Hz, 1H), 4.92 (d, J=7.8 Hz, 1H), 4.87 (d, J=6.0 Hz, 1H), 4.65 (t, J=5.4 Hz, 1H), 4.51 (d, J=4.8 Hz, 1H), 3.71-3.69 (m, 1H), 3.62-3.56 (m, 5H); $^{13}$C NMR (DMSO-$d_6$): 194.2, 159.8, 153.0, 130.5, 127.7, 126.7, 116.6, 100.5, 75.6, 73.2, 70.1, 68.1, 60.3).

1.3 Analysis of Urine and Renal Function

Serum blood urea nitrogen (BUN) and proteinuria were used to assess mice kidney function. Serum blood urea nitrogen (BUN) measurement of serum collected through the eye socket was done through a tester (Fuji DRI-CHEM 3000) with a test specimen (Fuju DRI-CHEM SLIDE). Determination of proteinuria was done by collecting urine samples and measuring urine protein content with protein concentration analyzing kit (BCA Protein Assay Kit, PIERCE) according to the manufacturer's instructions.

1.4 Pathologic Evaluation

To evaluate the renal histological changes, 10% formalin was used to fix the tissues, and sections were prepared and stained with hematoxylin and eosin (H&E) and observed under microscope. Changes in the tissues were analyzed by semi-quantitation. Items evaluated include: (1) cell density changes in glomerulus; (2) glomerulus fibrosis; (3) cell necrosis in glomerulus; (4) formation of crescent of glomerulonephritis. According to the ratio of glomeruli having pathological changes, 0 to 4 points were given as scores. 25 glomeruli were measured for each group and the sum of the points represents the renal histological changes. Secondly, mesenchymal and renal tubular atrophy, erythrocyte and protein granule sedimentation in renal tubules and mesenchymal inflammation were also evaluated.

In addition, to carry out immunohistochemistry (IHC) analysis, tissue fixation, paraffin-embedding, sectioning, rehydration and antigen retrieval were done with routine procedures, and 3% $H_2O_2$ was used to remove endogenous peroxidase. After reaction with blocking buffer for 1 hour, the tissues were reacted under 4° C. overnight with anti-mouse F4/80 antibodies (Serotec, UK), anti-mouse CD3 antibody (Dako, Denmark), anti-mouse NF-κB antibody (cell signaling, USA) respectively, and reacted with secondary antibody (Dako, Denmark) for 1 hour, visualized with diaminobenzidine (DAB) and nuclear background stained with hematoxylin. Light microscope (Olympus BX51) was used to observe the staining results. Observation was done under 400× field and photographs were taken.

1.5 Flow Cytometry Analysis

Mice spleens were taken out, grinded, rinsed and centrifuged to obtain spleen cells. To carry out mice inflammation reaction analysis, $1\times10^6$ cells were taken and reacted with anti-mouse CD3-FITC antibody, anti-mouse CD34-PE antibody anti-mouse CD8-PE, anti-mouse CD19-FITC antibody and anti-mouse CD69-PE antibody (all purchased from BD Pharmingen, CA) respectively in the dark under room temperature for 30 minutes, and analyzed with flow cytometry (Beckton Dickinson, Calif.).

1.6 Analysis of NF-κB p65 Activity in Kidney Tissues

Renal cortical tissues were taken and extracted for nuclear protein with nucleus extraction kit (Active Motif, Japan), and nuclear proteins were taken to detect NF-κB p65 activity after protein quantitation. TransAM NF-κB kit (Active Motif, Japan) was used for detection by ELISA according to the manual. Lastly, ELISA reader (Bio-Tek, USA) was used to detect OD 450 nm absorption and the values were converted to sample concentration according to the standard curve.

1.7 mRNA Real-Time PCR of Kidney Tissues

RNA was extracted from kidney tissues, reverse transcribed to cDNA and Real-Time PCR (Applied Biosystems) was carried out. Items determined include: IL-6, NLRP3, caspase-1, IL-1β and IL-18, where GAPDH gene expression levels were used to carry out the internal correction.

1.8 Protein Extraction and Western Blot Analysis

Renal cortical tissues were cut to pieces and placed in buffer, and grinding with sonication was used to lyse the cells. After centrifugation, the supernatant was preserved, and protein concentration was measured with protein concentration analyzing kit (BCA protein Assay Kit, PIERCE).

After the protein extract was separated by electrophoresis and blotted, primary anti-mouse NLRP3 (ENZO), caspase-1 (sc-514, Santa Cruz, USA), IL-1β (sc-7884, Santa Cruz, USA) antibodies were used to detect target proteins by Western blot analysis, where β-actin (Santa Cruz, USA) was used as the internal control. Secondary antibody was added, and chemiluminescence was used for visualization.

1.9 Enzyme-linked Immunosorbent Assay (ELISA)

Antibodies (anti-mouse IL-6 antibody and anti-mouse IL-1β antibody) were diluted according to the suggestion in the manufacturer's manual, and 100 μl antibodies were each added to all wells in a 96 well plate, reacted overnight, and added with samples or standard solution and reacted under room temperature for 3 hours, then added with HRP-linked specific antibody and reacted for 0.5 hours, and finally visualized with TMB. ELISA reader (Bio-Tek, USA) was used to detect OD 450 nm absorption and the values were converted to sample concentration according to the standard curve.

1.10 Kidney Tissue Protein Extraction and Western Blot Analysis

Nucleus protein extraction kit (Active Motif, USA) was used to extract cytoplasm and cell nuclear protein from kidney tissue hydrolysate. After the protein extract was separated by electrophoresis and blotted, primary anti-mouse Nrf2 (Santa Cruz, USA), COX-2 (Santa Cruz, USA), caspase-3 (Cell Signaling, USA) and caspase-9 (Cell Signaling, USA) antibodies were used to detect target proteins by Western blot analysis, where histone H3 (Cell Signaling, USA) and β-actin (Santa Cruz, USA) were used as the internal control for cell nucleus and cytoplasm respectively. Secondary antibody was added, and chemiluminescence was used for visualization.

1.11 Statistical Analysis

The results are presented as the mean±SEM. Comparison between two groups was performed using ANOVA or Student's t test. A value of $p<0.05$ was considered statistically significant.

Figure 1:
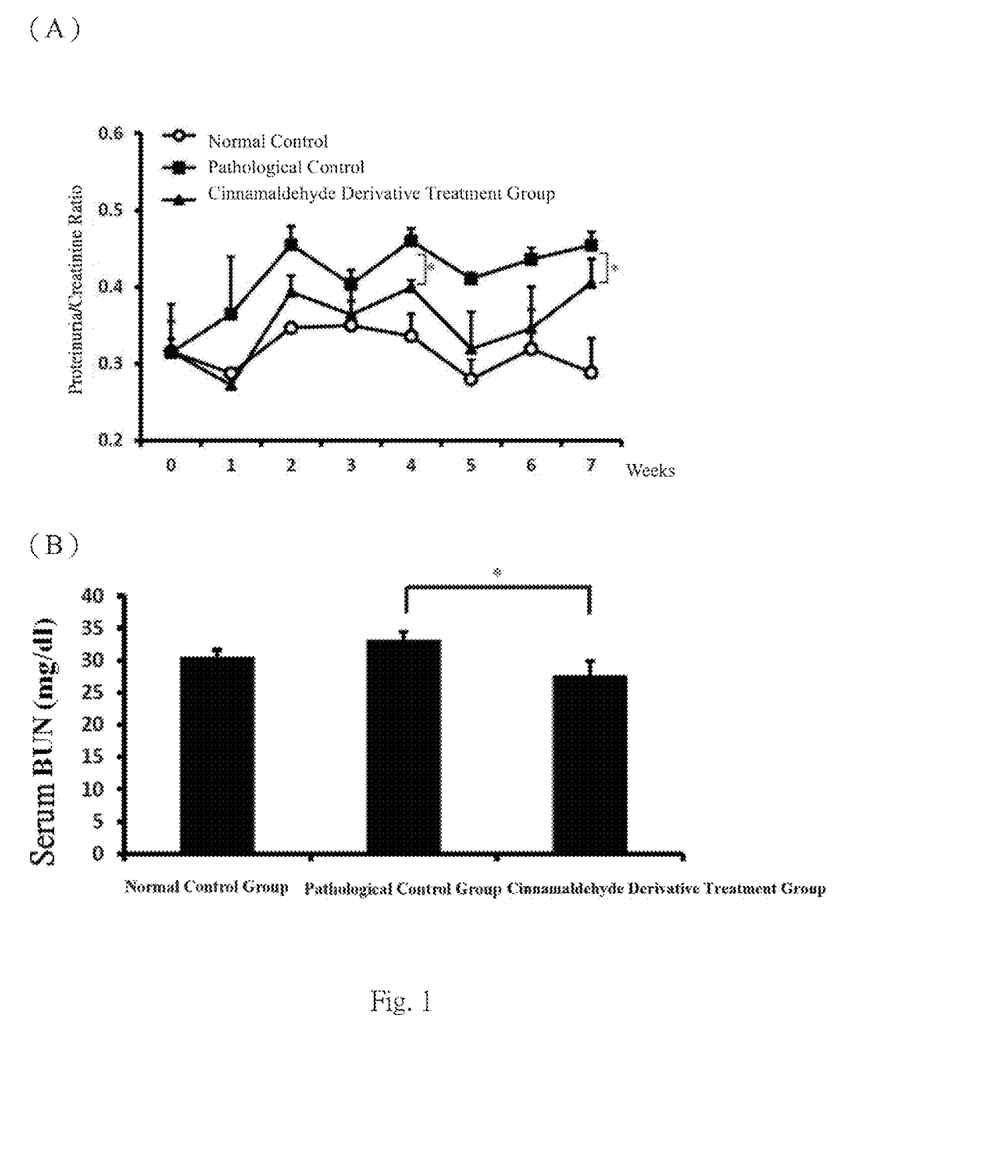
FIG. 1 shows changes of urine protein and renal function in GN mice treated with the hydroxycinammaldehde glycoside derivative of the present invention, including (A) urine protein/urine creatinine ratio and (B) serum blood urea nitrogen (BUN) level. *$p<0.05$.

2. Results 2.1 Cinnamaldehyde Derivative Ameliorated Pathological Syndromes in Mouse GN Model In LPS induced mouse GN model, proteinuria was continuously monitored to assess change in kidney function. FIG. 1 (A) shows the monitoring results of mouse urine protein content, where after LPS induced GN, urine protein content increased (disease group), which shows reduction of kidney function. In contrast, administration of cinnamaldehyde derivative can significantly ameliorate kidney function, reduce proteinuria, with statistical significance (*$p<0.05$). In addition, as shown in FIG. 1 (B), serum blood urea nitrogen (BUN) analysis shows that pathological control group mice had significantly increased amount of blood urea nitrogen; in contrast, GN disease treatment group by the cinnamaldehyde derivative of the invention had significantly lower blood urea nitrogen concentration, comparable to the normal control group.

Figure 2:
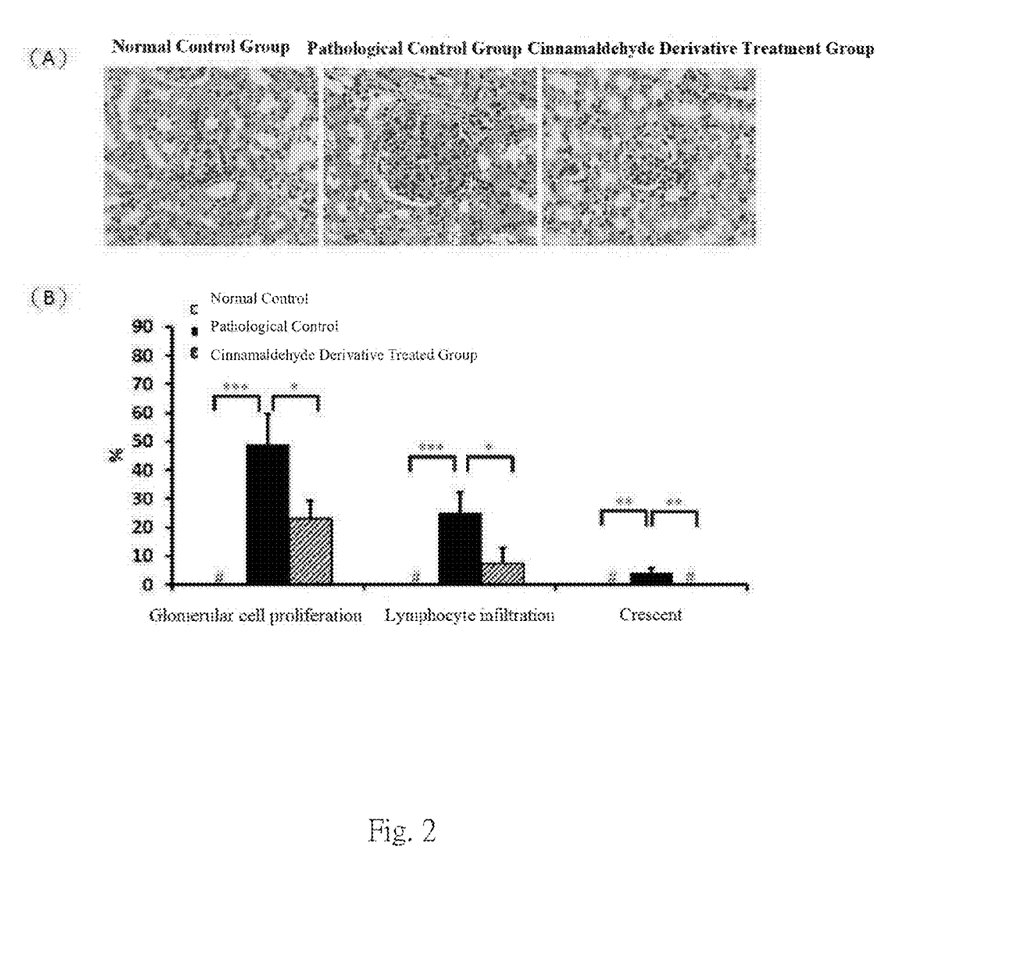
FIG. 2 shows the effects of the hydroxycinammaldehde glycoside of the present invention in ameliorating the renal histopathological lesions in GN mice, including (A) the staining results and (B) the quantitative analysis of glomerular cell proliferation, lymphocyte infiltration and crescent formation, in the normal control group, the GN disease control group (pathological control group), and the GN disease group treated by a hydroxycinammaldehde glycoside derivative (GN disease treatment group). *$p<0.05$, $p<0.01$, *$p<0.005$.

2.2 Cinnamaldehyde Derivative Reduces Proteinuria and Ameliorates Kidney Function in GN Mice In renal histology, glomeruli damages were visible in the GN disease group, including distinct glomerular proliferation, inflammatory cell infiltration, partial glomerular fibrosis, and crescent structure formation. After treatment by administering cinnamaldehyde derivative, glomerular proliferation was significantly ameliorated, lymphocyte infiltration was reduced, and no fibrosis condition occurrence was observed, see FIGS. 2 (A) and (B). These results show that cinnamaldehyde derivative can significantly reduce damaging conditions in glomeruli.

Figure 3:
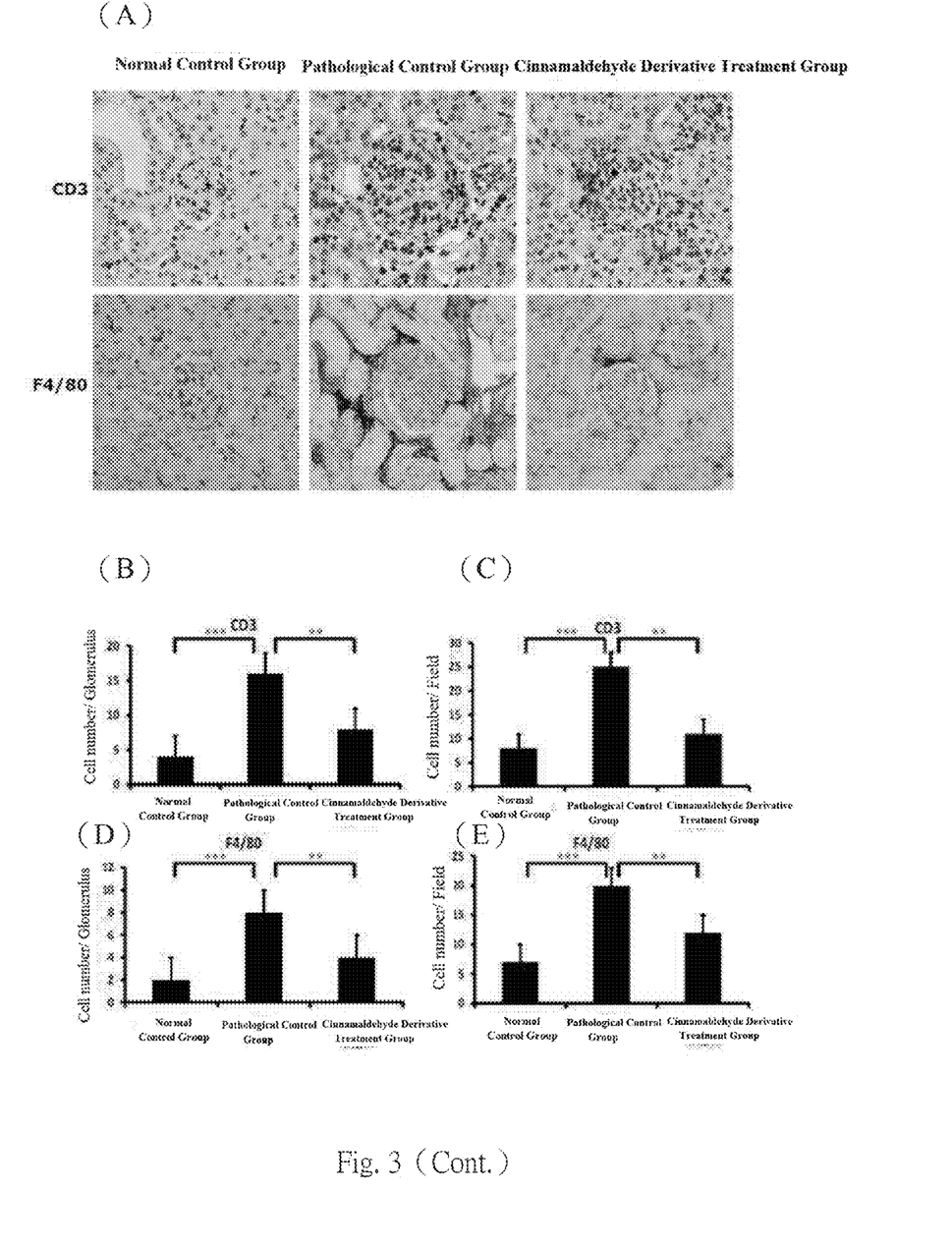
FIG. 3 shows the effects of the hydroxycinammaldehde glycoside of the present invention in reducing T cell infiltration and activation in GN mice, including (A) the staining results and (B)-(H) the corresponding quantitative analysis of specific T cells, in the normal control group, the GN disease control group (pathological control group), and the GN disease group treated by a hydroxycinammaldehde glycoside derivative (GN disease treatment group).

2.3 Hydroxycinnamaldehyde Derivative Reduces Infiltration of Inflammatory Cells 2.3.1 Reduction of Macrophage Deposits In the disease progression of nephritis, lymphocyte deposits will also cause macrophage gathering in hope of defense, which initiates a series of defensive reactions, but causes exacerbation of inflammatory conditions. Therefore, macrophage deposition condition in the kidney was evaluated by immunohistochemistry using macrophage marker F4/80. As shown in FIGS. 3 (A), (D) and (E), the GN disease group had more staining of macrophages which deposits in renal interstitium and renal periphery, wherein the macrophage staining was significantly less in the GN disease treatment group by the cinnamaldehyde derivative of the invention.

These results show that the cinnamaldehyde derivative of the invention can significantly reduce macrophage deposition.

2.3.2 Reduction of T Lymphocyte Infiltration and Activation

Flow cytometry was used to analyze T cell and B cell activation conditions in spleen cells. $CD3^+$ staining was used to represent T cells, as shown in FIG. 3 (F), T cell activation condition in the disease group was significantly higher than that of the normal control group (*$p>0.05$), when treated with cinnamaldehyde derivative, it showed the tendency of reduction. Helper T cells ($CD4^+$) activation ratio was further analyzed, as shown in FIG. 3 (G), it was higher in the disease group compared to the normal control group ($p<0.01$), and significantly ameliorated after treatment by the cinnamaldehyde derivative of the invention (*$p<0.005$). As for B cell ($CD19^+$) activation condition, as shown in FIG. 3 (H), there were no significant difference between the 3 groups.

In addition, T cell (CD3) infiltration in glomeruli was assessed by immunohistochemistry using kidney tissues kidney tissues, as shown in FIGS. 3(A), (B) and (C), it was found that more T lymphocyte infiltration was observed in the GN disease group, while T lymphocyte infiltration was significantly lowered after treatment by the cinnamaldehyde derivative of the invention.

These results showed that cinnamaldehyde derivative can significantly lower T lymphocyte infiltration and activation.

Figure 4:
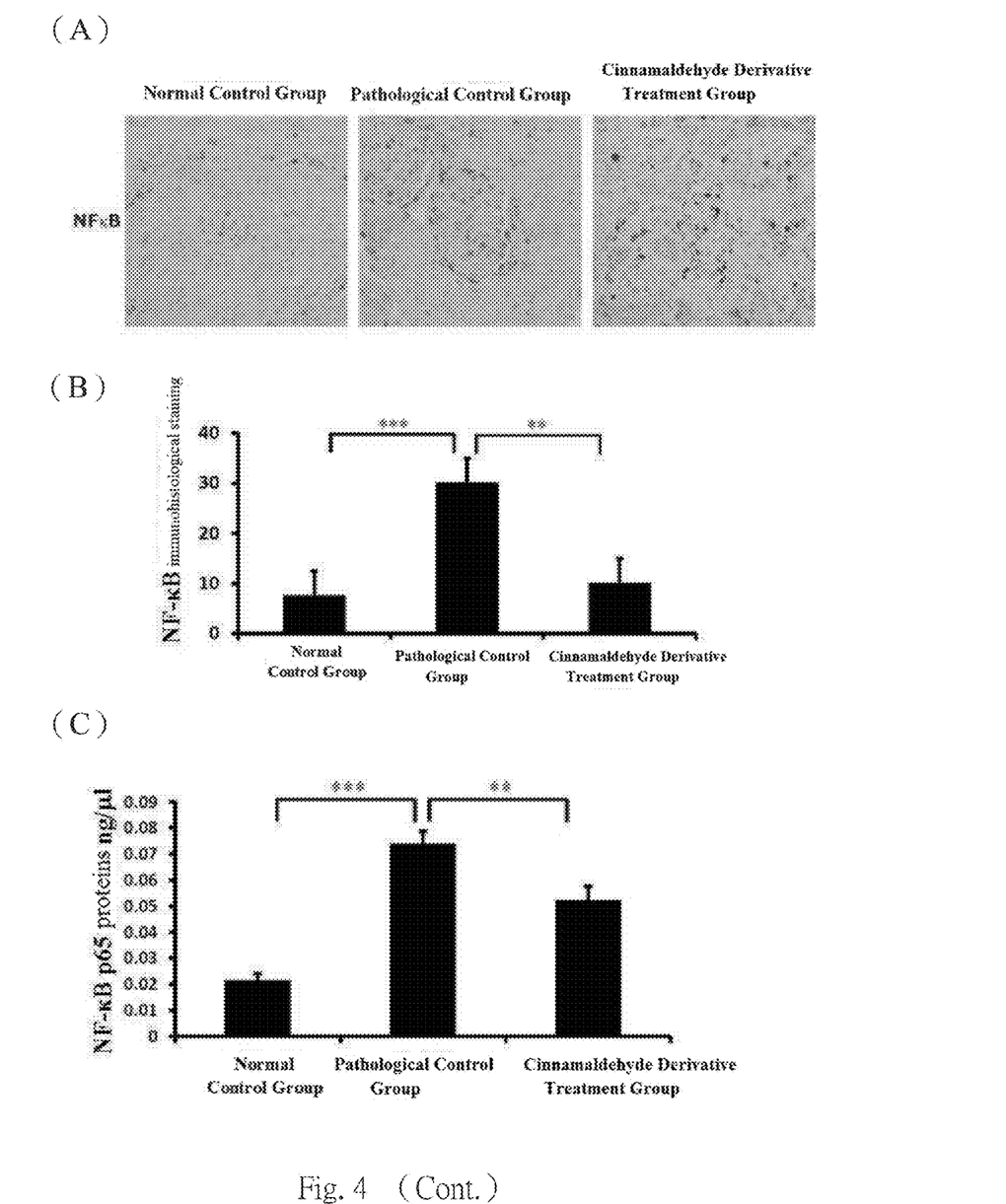
FIG. 4 shows the effects of the hydroxycinammaldehde glycoside of the present invention in suppressing expression of activated NF-κB and its downstream inflammatory cytokines, including (A) the staining results, (B) the corresponding quantitative analysis, (C) the NF-κB p65 content detected by enzyme-linked immunosorbent assay (ELISA), and (D) the ELISA result of IL-6 protein in the normal control group, the GN disease control group (pathological control group), and the GN disease group treated by a hydroxycinammaldehde glycoside derivative (GN disease treatment group).

2.4 Reduction of Activated NF-κB and its Downstream Inflammatory Cytokine Expression To analyze the functioning pathway of cinnamaldehyde derivative, NF-κB expression in kidney tissue was first observed by immunohistochemistry, where it was found that NF-κB expression in the disease group was significantly higher than that in the normal control group, where administration of cinnamaldehyde derivative can reduce its expression level, as shown in FIGS. 4 (A) and (B). Renal cortical proteins were further extracted and the NF-κB p65 content was detected with ELISA to evaluate NF-κB activation condition, as shown in FIG. 4 (C), NF-κB p65 expression in the disease group was significantly higher than that in the normal control group, indicating the activation of this signal transduction pathway, and administration of cinnamaldehyde derivative can lower its activation level.

Change in NF-κB mediated downstream pathway gene expression was then evaluated. IL-6 protein expression level in kidney tissue was detected by ELISA. As shown in FIG. 4 (D), IL-6 protein expression in the GN disease group were higher than that in the normal control group, which shows that LPS induced GN model can trigger inflammatory reaction by activating NF-κB signal transduction pathway. In contrast, treatment with cinnamaldehyde derivative can significantly suppress inflammatory reaction and reduce IL-6 expression.

These results show that the cinnamaldehyde derivative of the invention suppresses NF-κB activation and its downstream inflammatory cytokine expression in the kidney.

2.5 Suppression of NF-κB Downstream NLRP3 Inflammasome Activation and its Mediated Gene Expression NF-κB downstream NLRP3 inflammasome activation and its mediated caspase-1, IL-1β and IL-18 expression were further investigated.

Figure 5:
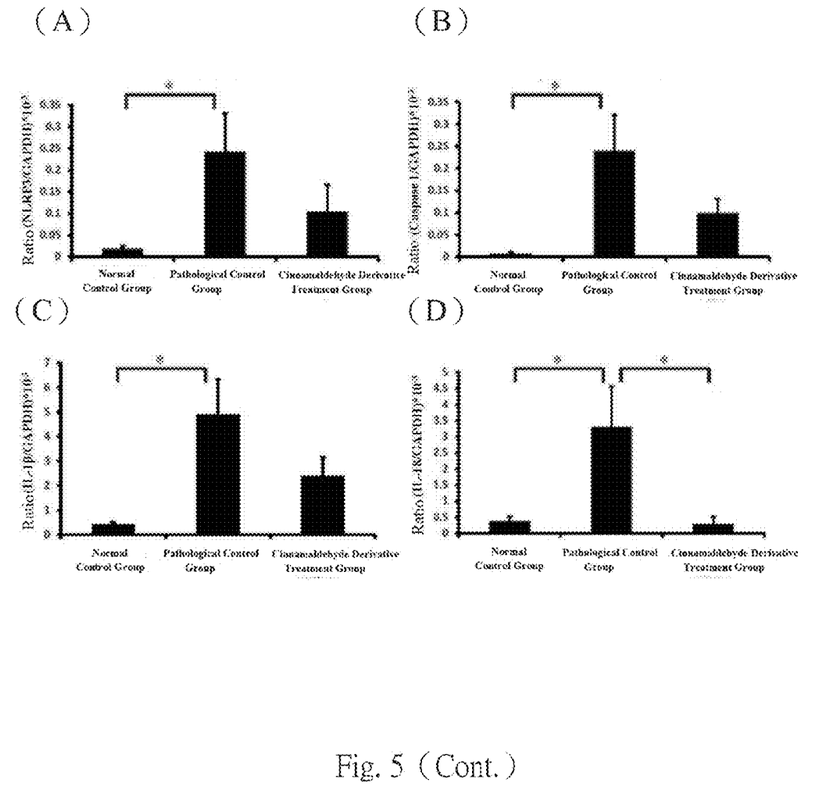
FIG. 5 shows the effects of the hydroxycinammaldehde glycoside of the present invention in suppressing activation of NLRP3 inflammasome (downstream to the NF-κB pathway) and expression of the genes mediated thereby, including (A)-(D) the real time PCR results, (E) the Western blot results, and (F)-(G) the semi-quantitative results of pro-caspase-1 and pro-interleukin (IL) 1-β, in the normal control group, the GN disease control group (pathological control group), and the GN disease group treated by a hydroxycinammaldehde glycoside derivative (GN disease treatment group). (H) ELISA result, mature IL-1β were significantly increased in GN disease group compared to hydroxycinammaldehde glycoside derivate treated GN group.

First, real-time PCR was used to evaluate NLPR3, caspase-1, IL-1β and IL-18 in kidney tissue. As shown in FIG. 5 (A)-(D), the expression level of said genes were detected to be significantly elevated in LPS induced GN animal model, and significantly reduced after treatment with cinnamaldehyde derivative.

Renal cortical proteins were extracted, and expression of the related proteins were further evaluated with Western blot and ELISA, the results are as shown in FIG. 5 (E)-(H).

Regarding caspase-1, pro-caspase-1 expression level was observed to be significantly increased, reduced after cinnamaldehyde derivative treatment, and matured caspase-1 expression level can also be observed to be higher in the disease group than in the cinnamaldehyde derivative treatment group. Mature caspase-1 will later cleave IL-1β. It was observed that pro-IL-1β had lower expression level in the disease group, which could be due to the activation of the related pathway causing pro-IL-1β to be cleaved into its mature state. As such, ELISA was used to observe the amount of mature IL-1β, which can be found that compared to the normal control group, the disease group had a significant increase, which significantly decreased after cinnamaldehyde derivative treatment.

These results show that the cinnamaldehyde derivative of the invention can suppress NF-κB downstream NLRP3 inflammasome activation and its mediated gene expression.

2.6 Suppression of Toll-Like Receptor 4 (TLR4) Activation (NF-κB Upstream)

Figure 6:
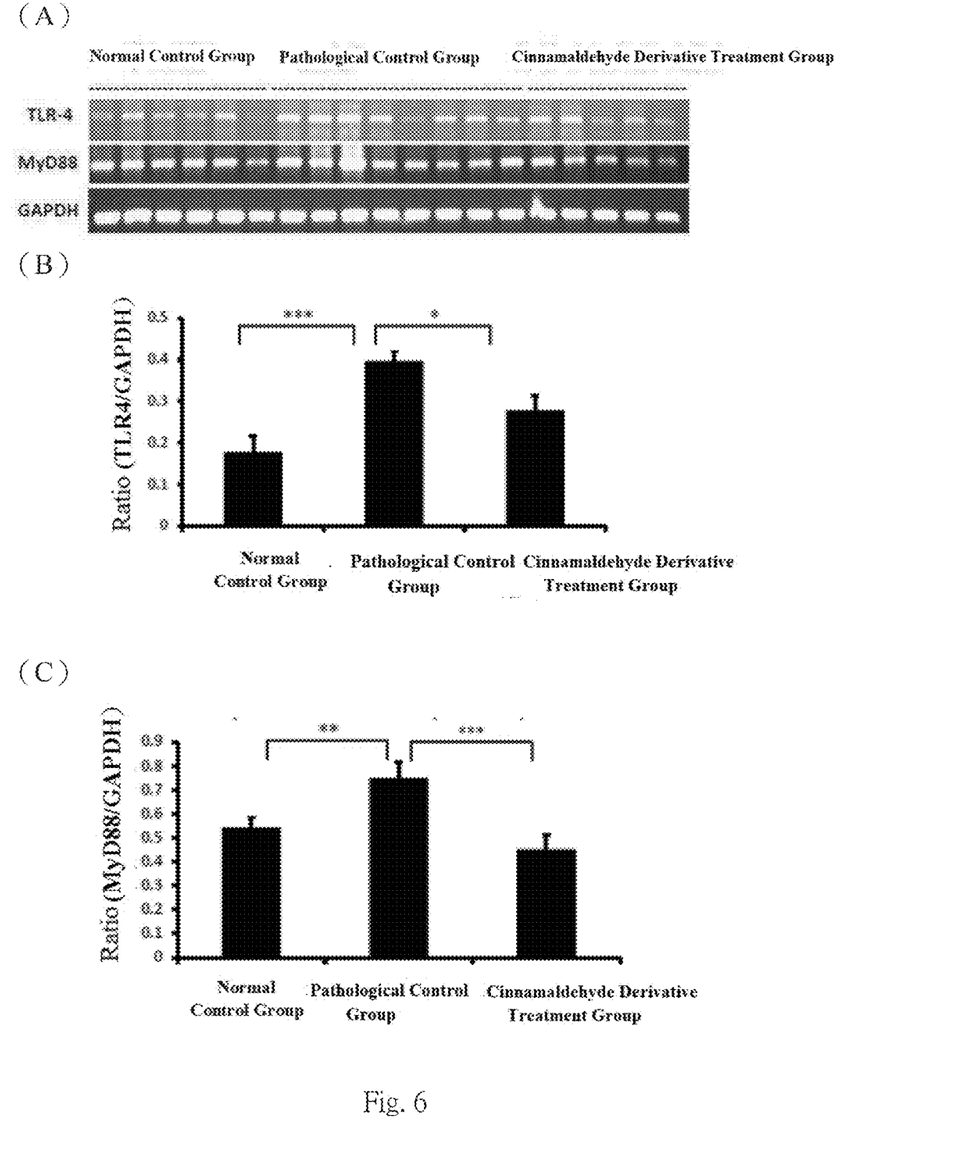
FIG. 6 shows the effects of the hydroxycinammaldehde glycoside of the present invention in suppressing activation of toll-like receptor 4 (TLR4) (upstream to the NF-κB pathway), including (A) mRNA expression results of TLR4 and its following adaptor MyD88, and (B)-(C) the corresponding quantitative analysis, in the normal control group, the GN disease control group (pathological control group), and the GN disease group treated by a hydroxycinammaldehde glycoside derivative (GN disease treatment group).

Reverse-transcription PCR was used to evaluate and semi-quantitate TLR4 and its following adaptin Myd88 mRNA expression. As shown in FIGS. 6 (A) and (B), TLR4 and MyD88 expression levels were higher in the disease group compared to the normal control group, and both were reduced after treatment with cinnamaldehyde derivative.

These results show that the cinnamaldehyde derivative of the invention can negatively affect activation of NF-κB downstream and the subsequent inflammatory protein expression by suppressing TLR4 pathway so as to achieve amelioration of inflammation.

2.7 Hydroxycinnamaldehyde Derivative Did not Cause Side-Effects

Figure 7:
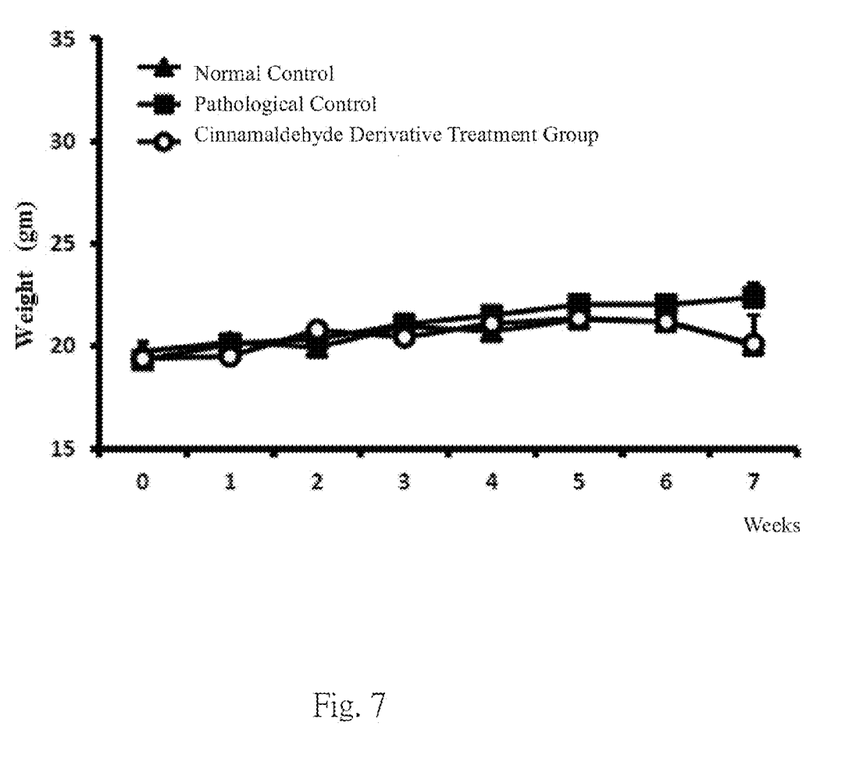
FIG. 7 shows that the hydroxycinammaldehde glycoside derivative of the present invention does not result in weight loss in animals, including the weight change in the normal control group, the GN disease control group (pathological control group), and the GN disease group treated by a hydroxycinammaldehde glycoside derivative (GN disease treatment group).

During the experiment processes, the drug safety of the cinnamaldehyde derivative was assessed through recording the weight change of mice each week. As shown in FIG. 7, mice administered with the hydroxycinnamaldehyde derivative also had stable increase in their bodyweight compared to the normal control group, indicating that the appetite or activity of the mice were not affected by the discomfort due to the drug administration. This result shows that the cinnamaldehyde derivative of the invention is safe since it did not cause obvious side-effects in animals.

3. Conclusion

The present invention provides a hydroxycinnamaldehyde glycoside derivative of formula (I). The present invention unexpectedly found that administering the hydroxycinnamaldehyde glycoside derivative of formula (I) to GN mice can significantly suppress the progression of the disease, including reduction of proteinuria and serum blood urea nitrogen (BUN), amelioration of kidney function, reduction of inflammatory cell-infiltration and glomerular proliferation. In the discussion of its mechanism, the hydroxycinnamaldehyde glycoside derivative can suppress NF-κB activation through the involvement of the TLR4 pathway to further reduce inflammatory cytokines thus alleviating symptoms of glomerulonephritis. In addition, studies also showed that the hydroxycinnamaldehyde glycoside derivative did not cause side-effects in animals.

Thus, the present invention discloses that the hydroxycinnamaldehyde glycoside derivative of formula (I) has an superior renoprotective effect in treating glomerulonephritis and ameliorating symptoms thereof. According to the present invention, the hydroxycinnamaldehyde glycoside derivative may be used as a medicament, which can be combined with medicaments that are presently available, to reduce the dosage and in turn the possible side effects, for treating glomerulonephritis.

It is generally believed that persons skilled in the art of the present invention should be able to utilize the present invention to its broadest scope based on the descriptions herein without further illustration. Therefore, it should be understood that the descriptions and claims provided herein are for illustration only but do not in any way limit the scope of the present invention.

What is claimed is:

1. A method for treating glomerulonephritis (GN) in a subject in need thereof, which comprises administering to the subject a therapeutically effective amount of a cinnamaldehyde derivative of formula (I) as follows Formula (I)

wherein R is a hexose or pentose moiety, which is not modified or further modified by oxidation, deoxidation, alkylation or acylation.

2. The method of claim 1, wherein R is glucose, fructose, galactose, rhamnose, ribose or glucuronic acid group.

3. The method of claim 1, wherein the method of treating is effective to reduce one or more kidney tissue lesions in GN in the subject selected from the group consisting of glomerular cell proliferation, inflammatory cell infiltration and fibrosis.

4. The method of claim 1, wherein the method of treating is effective to reduce one or more symptoms of GN in the subject selected from the group consisting of proteinuria and enhanced content of serum blood urea nitrogen (BUN).

5. The method of claim 1, wherein the cinnamaldehyde derivative is administered in combination with one or more therapeutic agents for treating glomerulonephritis selected from the group consisting of corticosteroid drugs, non-steriodal anti-inflammatory drugs (NSAIDs), immunosuppressants, cytotoxic drugs and vasodilators.

6. A cinnamaldehyde derivative of formula (I) as follows:

Formula (I)

wherein R is a hexose or pentose moiety, which is not modified or further modified by oxidation, deoxidation, alkylation or acylation.

7. The cinnamaldehyde derivative of claim 6, wherein R is a glucose, fructose, galactose, rhamnose, ribose or glucuronic acid group.

8. A pharmaceutical composition comprising a cinnamaldehyde derivative of formula (I) of claim 6 and a pharmaceutically acceptable carrier.

9. A pharmaceutical composition comprising a cinnamaldehyde derivative of formula (I) of claim 7 and a pharmaceutically acceptable carrier.

\* \* \* \* \*